US00PP15534P3

(12) United States Plant Patent
Winner

(10) Patent No.: US PP15,534 P3
(45) Date of Patent: Feb. 8, 2005

(54) ***GERANIUM* PLANT NAMED 'BALCOLREIM'**

(50) Latin Name: *Pelargonium peltatum*
Varietal Denomination: Balcolreim

(75) Inventor: Blair Winner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/741,699

(22) Filed: Dec. 19, 2003

(65) Prior Publication Data

US 2004/0226067 P1 Nov. 11, 2004

(51) Int. Cl.[7] ..... A01H 5/00

(52) U.S. Cl. ..... Plt./332

(58) Field of Search ..... Plt./332

*Primary Examiner*—Anne Marie Grunberg

(74) *Attorney, Agent, or Firm*—Wood, Phillips, Katz, Clark & Mortimer

(57) ABSTRACT

A new and distinct cultivar of *geranium* plant named 'Balcolreim', characterized by its semi-double 1-colored flowers, dark green-colored foliage and vigorous, mounded and cascading growth habit.

2 Drawing Sheets

Latin name of genus and species of plant claimed: *Pelargonium peltatum.*
Variety denomination: 'Balcolreim'.

BACKGROUND OF THE INVENTION

The present invention relates to a new and distinct cultivar of *geranium* plant botanically known as *Pelargonium peltatum* and hereinafter referred to by the cultivar name 'Balcolreim'.

The new cultivar originated in a controlled breeding program in Santa Paula, Calif., during December 1994. The purpose of the breeding program was the creation of *geranium* plants with vigorous upright mounded and cascading growth habits, dark green-colored foliage and new and unique flower colors.

The female parent of 'Balcolreim' was the cultivar 'Butterfly' (not patented). The male parent of 'Balcolreim' was the proprietary *Pelargonium peltatum* selection designated '90777-5' (not patented). The new *geranium* was discovered and selected by the inventor as a single flowering plant from within the progeny of the above stated cross-pollination during June 1995 at Santa Paula, Calif. and was initially designated '16769-2B'.

Asexual reproduction of the new *geranium* by terminal stem cuttings since 2001 at Arroyo Grande, Calif. and West Chicago, Ill., has demonstrated that the new *geranium* reproduces true to type, with all characteristics as herein described, firmly fixed and retained through successive generations of such asexual propagation.

SUMMARY OF THE INVENTION

The new *geranium* has not been observed under all possible environmental conditions to date. Accordingly, it is possible that the phenotype may vary somewhat with variations in the environment, such as temperature, light intensity, and day length, without, however, any variance in genotype.

It was repeatedly found that the cultivar of the present invention:

1. Forms semi-double red-colored flowers,
2. Forms dark green-colored foliage, and
3. Exhibits a vigorous mounded and cascading growth habit.

Plants of the new cultivar differ from plants of the female parent and plants of the male parent '90777-5' primarily in flower color.

Of the many *geranium* cultivars known to the inventor, the most similar in comparison to 'Balcolreim' is 'Balcolred', disclosed in U.S. Plant patent application Ser. No. 10/099,261 (abandoned). However, in side-by-side comparisons, plants of 'Balcolreim' exhibit larger umbels and smaller leaves than the plants of 'Balcolred'.

BRIEF DESCRIPTION OF THE DRAWINGS

The accompanying photographic drawings show as nearly true as it is reasonably possible to make the same in color illustrations of this type, typical flower and foliage characteristics of the new cultivar. Colors in the photographs differ slightly from color values cited in the detailed description, which accurately describes the colors of 'Balcolreim'. The plants were grown for 8 weeks in a greenhouse at West Chicago, Ill.

DETAILED BOTANICAL DESCRIPTION

Figure 1:
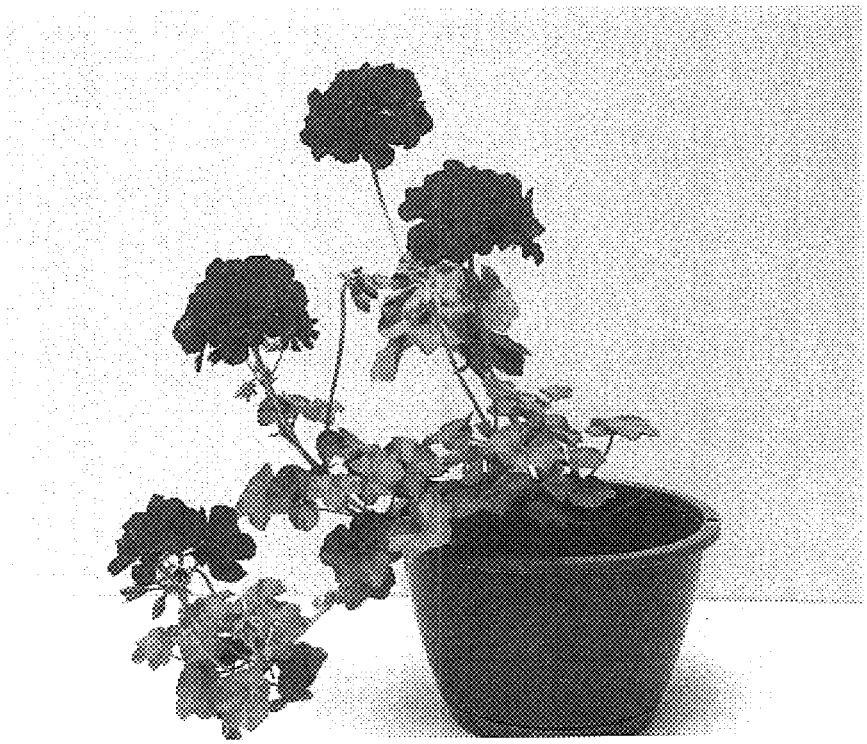
FIG. 1 illustrates a side view of the overall growth and flowering habit of 'Balcolreim'.
Figure 2:
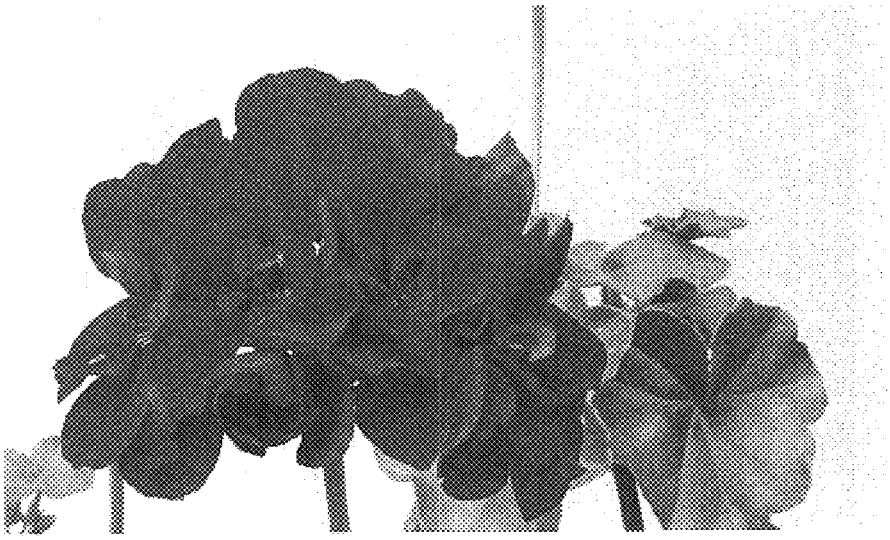
FIG. 2 illustrates a close-up view of a single umbel of 'Balcolreim'.
Figure 3:
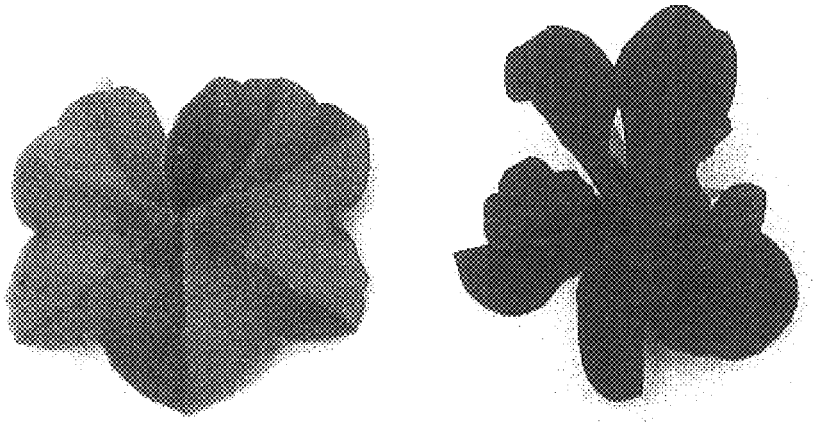
FIG. 3 illustrates a close-up view of a single flower and leaf of 'Balcolreim'.

The chart used in the identification of colors described herein is The R.H.S. Colour Chart of The Royal Horticultural Society, London, England 1995 edition, except where color terms of ordinary significance are used. The color values were determined on Aug. 13, 2003 in West Chicago, Ill. The readings were taken between 10:00 and 11:45 a.m. under natural light conditions.

The plants used for the following measurements and descriptions were produced from cuttings taken from stock plants and grown in a double polycarbonate-covered greenhouse under conditions comparable to those used in commercial practice. The plants were grown in 10 cm pots for 8 weeks utilizing a soilless growth medium. Greenhouse temperatures were maintained at approximately 65°–70° F. (18°–21° C.) during the day and approximately 60°–65° F. (15°–18° C.) during the night. Greenhouse light levels of 4,000 to 6,000 footcandles were maintained during the day. Plants were pinched at three weeks after planting.

Classification:

*Botanical.*—*Pelargonium peltatum* cultivar 'Balcolreim'.

*Commercial.*—Ivy *geranium.*

Parentage:

*Female parent.*—*Pelargonium peltatum* cultivar 'Butterfly'.

*Male parent.*—Proprietary *Pelargonium peltatum* selection designated '90777-5'.

Propagation:

*Type cutting.*—Terminal stem.

*Time to initiate roots.*—Approximately 10 to 14 days.

*Time to develop roots.*—Approximately 21 to 28 days.

*Root description.*—Fibrous.

*Rooting habit.*—Well branched.

Plant description:

*General appearance and growth habit.*—Vigorous, mounded and cascading.

*Height above pot.*—Including inflorescences: Approximately 25.3 cm.

*Width/area of spread.*—Approximately 38.9 cm.

*Branching habit.*—Freely basal branching. Approximately 3 branches per plant. Pinching 14 to 21 days after transplanting helps to improve basal branching.

*Branch description.*—Length: Approximately 20.7 cm. Diameter: Approximately 4.3 mm. Color: 144A. Texture: Moderately sericeous. Internode length at center of branch: Approximately 3.4 cm.

*Foliage description.*—Form: Simple. Arrangement: Opposite. Number of leaves per lateral branch: Approximately 9.4. Shape: Palmately lobed. Margin: Widely crenate. Apex: Obtuse. Base: Cordate, overlapping. Venation pattern: Palmate. Size: Mature leaf length: Approximately 4.4 cm. Mature leaf width: Approximately 7.8 cm. Upper surface texture: Moderately pubescent. Lower surface texture: Moderately pubescent with dense pubescence along veins. Color of mature foliage — Upper surface: 146A with veins of 146D and zone of 200B. Color of mature foliage — Lower surface: 146B with veins of 146D. Petiole length: Approximately 5 cm. Petiole diameter. Approximately 1.7 mm. Petiole Texture: Moderately sericeous. Petiole color: 146A.

Flowering description:

*Outdoor flowering habit.*—'Balcolreim' is freely flowering under outdoor growing conditions with substantially continuous blooming from spring through fall.

*Time of first flower.*—Approximately 8 weeks after planting of rooted cutting.

*Lastingness of individual bloom.*—Approximately 5–7 days.

Inflorescence description:

*Type.*—Hemispherical umbel. Position: Above foliage. Number of open umbels at any one time: Three. Number of developing umbels at any one time: Three. Fully open umbel: Diameter: Approximately 9.5 cm. Height/depth: Approximately 5.6 cm. Number of flowers per umbel: Approximately 8.7.

*Peduncle.*—Strong, erect. Length: Approximately 15.1 cm. Diameter: Approximately 3 mm. Texture: Moderately sericeous. Color: 144A.

Flower description:

*Bud just before opening.*—Shape: Elliptic. Length: Approximately 1.7 cm. Diameter: Approximately 8.2 mm. Petal color: 45A. Sepal color: 144A with streaks of 173A.

*Corolla.*—Form: Semi-double. Shape: Round, slightly cupped. Diameter/Width: Approximately 5.2 cm. Depth: Approximately 1.8 cm. Fragrance: None. Persistent.

*Petals/petaloids.*—Quantity: Approximately 8 petals and 5 petaloids per flower. Arrangement: Imbricate. Shape: Obovate. Apex: Obtuse. Base: Attenuate. Margin: Entire. Texture of upper and lower surface: Glabrous. Length of upper two petals: Approximately 3 cm. Width of upper two petals: Approximately 2.1 cm. Length of lower petals: Approximately 2.7 cm. Width of lower petals: Approximately 1.9 cm. Color of all petals: Fully opened, upper surface: 45B with veins of 187A on upper petals. Fully opened, lower surface: 45C.

*Pedicel.*—Strength: Strong. Angle: Erect. Length: Approximately 2.6 cm. Diameter: Approximately 2 mm. Texture: Moderately sericeous. Color: 144A.

*Sepals.*—Quantity per flower: 5. Shape: Elliptic. Tip: Acuminate. Base: Truncate. Margin: Entire. Length of largest sepal: 1.5 cm. Width of largest sepal: 5 mm. Length of smallest sepal: 1.5 cm. Width of smallest sepal: 2 mm. Texture of all sepals: Upper surface (inside): Glabrous. Lower surface (outside): Puberulent. Color of all sepals: Upper and lower surface: 144A with streaks of 173A.

*Reproductive organs.*—Androecium: Stamen number: Approximately 9 per flower. Filament color: N155. Anther quantity: Approximately 9. Anther length: Approximately 2 mm. Immature anther color: 52B. Mature anther color: N187A. Pollen amount: Moderate. Pollen color 169C. Gynoecium: Pistil quantity: One per flower. Pistil length: Approximately 12 mm. Stigma shape: 5 pointed star. Stigma length: 4 mm. Stigma color: 187B. Style length: 3 mm. Style color: 154D. Ovary length: 5 mm. Ovary diameter: 2 mm. Ovary texture: Sericeous. Ovary color: 143B.

Seed and fruit production: Neither seed nor fruit production has been observed.

Disease and pest resistance: Resistance to diseases and pests common to *geraniums* has not been observed.

Hardiness zone: 'Balcolreim' is presumably hardy in zones nine (9) and above.

What is claimed is:

1. A new and distinct cultivar of *geranium* plant named 'Balcolreim' substantially as herein shown and described, which:

1. Forms semi-double red-colored flowers,
2. Forms dark green-colored foliage, and
3. Exhibits a vigorous mounded and cascading growth habit.

* * * * *